US012569140B2

(12) United States Patent
Sherlock et al.

(10) Patent No.: US 12,569,140 B2
(45) Date of Patent: Mar. 10, 2026

(54) FIBER-BASED MULTIMODAL BIOPHOTONIC IMAGING AND SPECTROSCOPY SYSTEM

(71) Applicant: The Regents of the University of California, Oakland, CA (US)

(72) Inventors: Benjamin E. Sherlock, Davis, CA (US); Diego R. Yankelevich, Davis, CA (US); Julien Bec, Davis, CA (US); Laura Marcu, Davis, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 638 days.

(21) Appl. No.: 17/950,994

(22) Filed: Sep. 22, 2022

(65) Prior Publication Data

US 2023/0024540 A1 Jan. 26, 2023

Related U.S. Application Data

(63) Continuation of application No. 16/500,374, filed as application No. PCT/US2018/027372 on Apr. 12, 2018, now Pat. No. 11,490,818.

(60) Provisional application No. 62/485,181, filed on Apr. 13, 2017.

(51) Int. Cl.

| | |
|---|---|
| ***A61B 5/00*** | (2006.01) |
| ***A61B 3/10*** | (2006.01) |
| *G01B 9/02091* | (2022.01) |
| *G01N 21/64* | (2006.01) |

(52) U.S. Cl.
CPC ............ *A61B 5/0086* (2013.01); *A61B 3/102* (2013.01); *A61B 5/0066* (2013.01); *G01B 9/02091* (2013.01); *G01N 21/6458* (2013.01); *G01N 2021/6484* (2013.01)

(58) Field of Classification Search
CPC ................ A61B 5/0071; A61B 5/0066; G01N 21/6486; G01N 2021/6484
See application file for complete search history.

(56) References Cited

U.S. PATENT DOCUMENTS

| | | | | |
|---|---|---|---|---|
| 7,590,324 B1 * | 9/2009 | Chen | G02B 6/02342 385/127 |
| 2011/0026035 A1 * | 2/2011 | Muto | A61B 3/102 356/450 |
| 2012/0101374 A1 * | 4/2012 | Tearney | A61B 5/6852 600/425 |

* cited by examiner

*Primary Examiner* — Rajeev P Siripurapu
(74) *Attorney, Agent, or Firm* — MARSHALL, GERSTEIN & BORUN LLP

(57) ABSTRACT

The disclosed embodiments relate to multimodal imaging system comprising a fiber-coupled fluorescence imaging system, which operates based on ultra-violet (UV) excitation light, and a fiber-coupled optical coherence tomography (OCT) imaging system. The multimodal imaging system also includes a fiber optic interface comprising a single optical fiber, which facilitates light delivery to a sample-of-interest and collection of returned optical signals for both the fluorescence imaging system and the OCT imaging system. During operation of the system, the single optical fiber carries both UV light and coherent infrared light through two concentric light-guiding regions, thereby facilitating generation of precisely co-registered optical data from the fluorescence imaging system and the OCT imaging system.

9 Claims, 10 Drawing Sheets

GERMANIUM-
DOPED SILICA
206

PURE
SILICA
204

DOUBLE-CLAD
FIBER
200

FLUORINE-DOPED
SILICA OR A LOW-
INDEX POLYMER
202

UV
LIGHT
210

LAUNCH
CONDITION
212

204

206

DOUBLE-CLAD FIBER 200

PURE
SILICA
308

FLUORINE-DOPED
SILICA OR A LOW-
INDEX POLYMER
302

PURE
SILICA
304

FLUORINE-DOPED
SILICA
306

START

USE A FIBER-COUPLED FLUORESCENCE IMAGING SYSTEM, WHICH OPERATES BASED ON UV EXCITATION LIGHT, TO GATHER A FLUORESCENCE EMISSION FROM A SAMPLE-OF-INTEREST
702

CONCURRENTLY USE A FIBER-COUPLED OPTICAL COHERENCE TOMOGRAPHY (OCT) IMAGING SYSTEM TO ACQUIRE DEPTH-RESOLVED IMAGES OF THE SAMPLE-OF-INTEREST
704

DURING OPERATION OF THE COMBINED SYSTEM, DIRECT LIGHT FOR BOTH THE FLUORESCENCE IMAGING AND THE OCT IMAGING THROUGH A SINGLE DOUBLE-CLAD OPTICAL FIBER, WHICH FACILITATES LIGHT DELIVERY TO THE SAMPLE-OF-INTEREST AND COLLECTION OF ASSOCIATED RETURNED OPTICAL SIGNALS, WHEREIN THE SINGLE OPTICAL FIBER CARRIES BOTH UV LIGHT FOR THE FLUORESCENCE IMAGING AND INFRARED LIGHT FOR THE OCT IMAGING THROUGH TWO CONCENTRIC LIGHT-GUIDING REGIONS, THEREBY FACILITATING GENERATION OF PRECISELY CO-REGISTERED OPTICAL DATA FROM THE FLUORESCENCE IMAGING SYSTEM AND THE OCT IMAGING SYSTEM
706

END

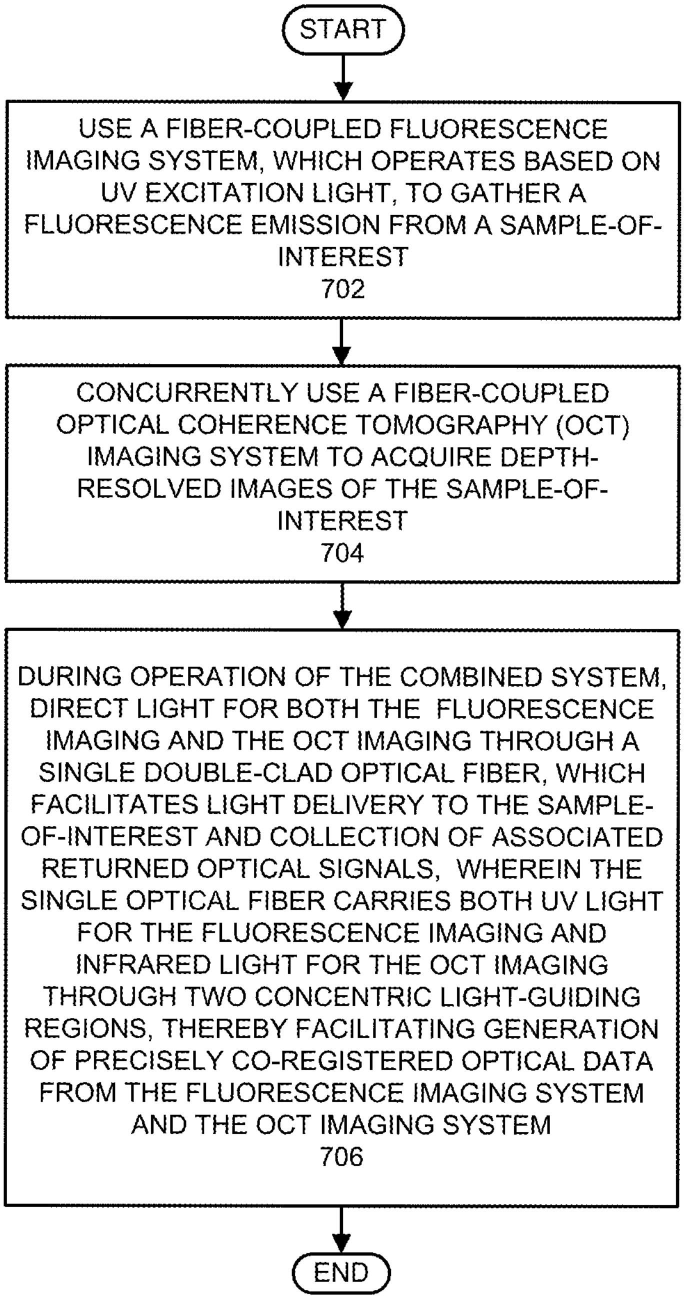

FIG. 7

FIBER-BASED MULTIMODAL BIOPHOTONIC IMAGING AND SPECTROSCOPY SYSTEM

RELATED APPLICATION

This application is a continuation of, and hereby claims priority under 35 U.S.C. § 120 to, pending U.S. patent application Ser. No. 16/500,374, which was filed 2 Oct. 2019. Also, this application claims priority under 35 U.S.C. § 119 to U.S. Provisional Application No. 62/485,181, entitled "Fiber-Based Multimodal Biophotonic Imaging and Spectroscopy Platform" by the same inventors as the instant application, which was filed 13 Apr. 2017. Contents of the preceding applications are incorporated herein by reference.

GOVERNMENT LICENSE RIGHTS

This invention was made with United States government support under Grant No. 1R21 CA178578-1 awarded by the National Institute of Health. The United States government has certain rights in the invention.

BACKGROUND

Field

The disclosed embodiments relate to techniques for characterizing biological materials by analyzing laser-induced light emissions. More specifically, the disclosed embodiments relate to a multimodal biophotonic imaging system, which provides both optical coherence tomography (OCT) imaging and fluorescence lifetime imaging (FLIm) modalities through a single double-clad optical fiber.

Related Art

Optical imaging techniques are widely used in various medical applications to analyze tissue structure and to characterize the biochemical composition of tissues. However, the complexity of the optical tissue response makes it challenging for a single imaging modality to accurately characterize tissue structure and function. Multimodal imaging platforms, which combine two or more modalities in a single apparatus, aim to combine the strengths of complimentary imaging techniques to sample a larger cross-section of the optical tissue response. Fluorescence lifetime imaging (FLIm) and optical coherence tomography (OCT) are two such complimentary imaging modalities. Fluorescence lifetime is a functional imaging technique, which uses the temporal dynamics of fluorescence emission to delineate regions of biochemical contrast on a sample. (See Chang, C W; Sud, D; Mycek, M A (2007). "Fluorescence lifetime imaging microscopy". *Methods in cell biology.* 81:495-524.) In contrast, optical coherence tomography uses phase-sensitive measurements of ballistically scattered photons to acquire depth resolved images of sample microstructure. (See Huang, D; Swanson, E A; Lin, C P; Schuman, J S; Stinson, W G; Chang, W; Hee, M R; Flotte, T; et al. (1991). "Optical Coherence Tomography." Science. 254 (5035): 1178-81.) The benefits of combining FLIm and OCT in a single apparatus have been exploited by several research groups, who implemented multimodal imaging platforms that were based around a conventional microscope frame. Although these pioneering efforts were successful, the use of bulky free-space optics prevented their use in applications where the imaging geometry is highly restricted, such as the intravascular environment or inside a tissue bioreactor.

Optical fibers are widely used in biophotonics applications to provide a narrow and flexible interface between a limited-access region of a sample and the imaging apparatus. No existing system has combined both FLIm and OCT imaging modalities through an optical fiber interface. It is impractical to use separate fibers for the two different imaging modalities because of problems related to interface flexibility, and challenges in combining and registering the signals at a probe. Moreover, it is also difficult to channel both short-wavelength ultraviolet (UV) FLIm signals and longer-wavelength OCT signals and through the same optical fiber.

Hence, what is needed is an optical imaging system, which combines both UV-wavelength optical fluorescence and OCT imaging modalities in a system that operates through a single optical fiber.

SUMMARY

The disclosed embodiments relate to multimodal imaging system, comprising: a fiber-coupled fluorescence imaging system, which operates based on ultra-violet (UV) excitation light; and a fiber-coupled optical coherence tomography (OCT) imaging system. The multimodal imaging system also includes a fiber optic interface comprising a single optical fiber, which facilitates light delivery to a sample-of-interest and collection of returned optical signals for both the fluorescence imaging system and the OCT imaging system. During operation of the system, the single optical fiber carries both UV light and coherent infrared light through two concentric light-guiding regions, thereby facilitating generation of precisely co-registered optical data from the fluorescence imaging system and the OCT imaging system.

In some embodiments, the single optical fiber is a double-clad optical fiber, comprising: (1) a single-mode central core composed of high-index doped silica, which carries the coherent infrared light; (2) a multimode inner cladding composed of pure silica surrounding the central core, which carries the UV excitation light, wherein the UV excitation light is guided into the inner cladding so that the UV excitation light circulates around the central core, thereby minimizing interactions with the central core and thereby minimizing associated transmission losses and autofluorescence; and (3) an outer cladding composed of a low-index material, such as doped silica or a low index-polymer, surrounding the inner cladding.

In a variation on these embodiments, infrared light for the OCT imaging system is transmitted through the single-mode central core.

In some embodiments, the single optical fiber is a double-clad fiber, comprising: (1) a single-mode central core composed of pure silica surrounded by a ring of low-index doped silica; (2) a multimode inner cladding composed of pure silica surrounding the central single-mode core; and (3) an outer cladding composed of a low-index material, such as doped silica or a low index-polymer, surrounding the inner cladding.

In a variation on these embodiments, the infrared light for the OCT imaging system is transmitted through the central core, and the UV excitation light for the fluorescence imaging system is transmitted through the inner cladding.

In a variation on these embodiments, both the UV excitation light for the fluorescence imaging system and the infrared light for the OCT imaging system are transmitted through the central core, and the returned light for the fluorescence imaging system is transmitted through the multimode inner cladding to enable higher optical resolution fluorescence lifetime imaging (FLIm).

In some embodiments, the fluorescence imaging system comprises a time-resolved FLIm system.

In some embodiments, the UV excitation light has a wavelength less than 400 nm.

In some embodiments, the multimodal imaging system provides an optical architecture that allows structural and functional imaging modalities to operate independently and in parallel.

In some embodiments, the multimodal imaging system provides an optical architecture that facilitates switching between high and low optical resolutions.

BRIEF DESCRIPTION OF THE FIGURES

FIG. 7 presents a flow chart for the process of operating a combined fluorescence and OCT imaging system, which transmits light through a single optical fiber, in accordance with the disclosed embodiments.

DETAILED DESCRIPTION

The following description is presented to enable any person skilled in the art to make and use the present embodiments, and is provided in the context of a particular application and its requirements. Various modifications to the disclosed embodiments will be readily apparent to those skilled in the art, and the general principles defined herein may be applied to other embodiments and applications without departing from the spirit and scope of the present embodiments. Thus, the present embodiments are not limited to the embodiments shown, but are to be accorded the widest scope consistent with the principles and features disclosed herein.

The data structures and code described in this detailed description are typically stored on a computer-readable storage medium, which may be any device or medium that can store code and/or data for use by a computer system. The computer-readable storage medium includes, but is not limited to, volatile memory, non-volatile memory, magnetic and optical storage devices such as disk drives, magnetic tape, CDs (compact discs), DVDs (digital versatile discs or digital video discs), or other media capable of storing computer-readable media now known or later developed.

The methods and processes described in the detailed description section can be embodied as code and/or data, which can be stored in a computer-readable storage medium as described above. When a computer system reads and executes the code and/or data stored on the computer-readable storage medium, the computer system performs the methods and processes embodied as data structures and code and stored within the computer-readable storage medium. Furthermore, the methods and processes described below can be included in hardware modules. For example, the hardware modules can include, but are not limited to, application-specific integrated circuit (ASIC) chips, field-programmable gate arrays (FPGAs), and other programmable-logic devices now known or later developed. When the hardware modules are activated, the hardware modules perform the methods and processes included within the hardware modules.

Multimodal Imaging System

The disclosed embodiments provide a multimodal simultaneous FLIm and OCT imaging platform, which uses a single optical fiber interface. Note that the combination of two modalities in a single optical fiber places stringent requirements on the fiber itself. OCT requires light to be guided in a single spatial mode, whereas FLIm benefits greatly from the increased fluorescence collection cross-section given by multimode fibers. To accommodate these requirements a double clad fiber is used, which combines a central single-mode core and surrounding multimode inner cladding in single, concentric fiber package.

Figure 2A:
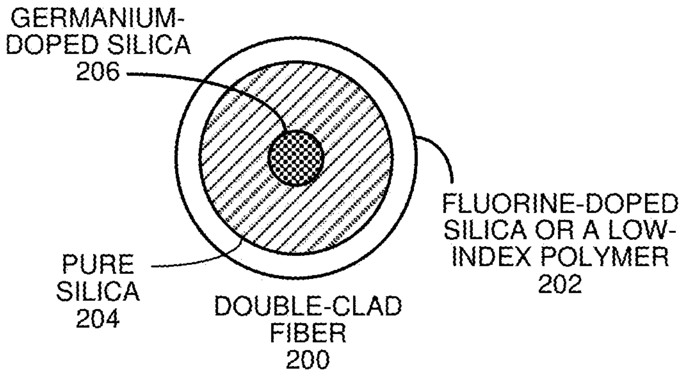
FIG. 2A illustrates a cross-sectional view of a dual-clad optical fiber in accordance with the disclosed embodiments.

To meet the requirements of this multimodal imaging system, two-meter sections of low cost, commercially available double-clad fiber (DCF) were used. In the embodiment illustrated in FIG. 2A, the DCF 200 comprises a high-index, Germanium-doped silica central core 206 and a pure silica multimode inner cladding 204 with diameters of 11.5 μm and 400 μm, respectively. The inner cladding 204 is surrounded by an outer cladding 202 composed of a low-index material, such as fluorine-doped silica or a low index-polymer, so the resulting outer diameter of the fiber is 550 μm. The core and inner cladding numerical apertures (NA) are 0.08 and 0.46, respectively. The distal end of the DCF was imaged on the sample using a 1.8 mm diameter, lithium-ion exchange gradient-index lens with an NA of 0.2.

Figure 2B:
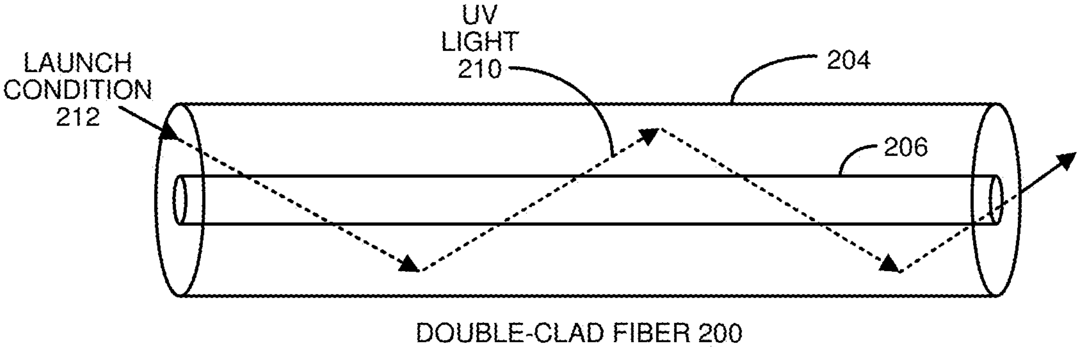
FIG. 2B illustrates light circulating through a silica inner cladding around a high-index Germanium-doped silica optical core in accordance with the disclosed embodiments.

Referring to FIG. 2B, in order to minimize interactions between UV light 210 travelling through inner cladding 204 and central core 206, UV light 210 is directed into inner cladding 204 with a launch condition 212 that ensures that the UV light 210 circulates around central core 206 instead of impacting central core 206. This minimizes interactions with central core 206 and thereby minimizes associated transmission losses.

Figure 3:
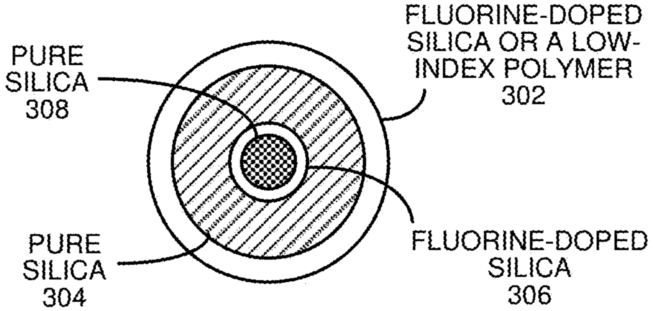
FIG. 3 illustrates a cross-sectional view of another dual-clad optical fiber, which surrounds the pure silica optical core with fluorine-doped silica in accordance with the disclosed embodiments.

In the alternative embodiment illustrated in FIG. 3, the DCF comprises a pure silica single-mode central core 308 surrounded by a ring of low-index Fluorine-doped silica 306. The central core 308 and surrounding ring 306 are enclosed by a pure silica inner cladding 304, which is itself enclosed by an outer cladding 302, which is composed of a low-index material, such fluorine-doped silica or a low-index polymer. In this embodiment, the surrounding ring of a ring of doped silica 306 eliminates interference between light propagating in the central core 308 and the inner cladding. Hence, in this embodiment, it is not necessary to guide the light in the inner cladding 304 to circulate around central core 308 to minimize unwanted interactions that lead to transmission losses.

Figure 1A:
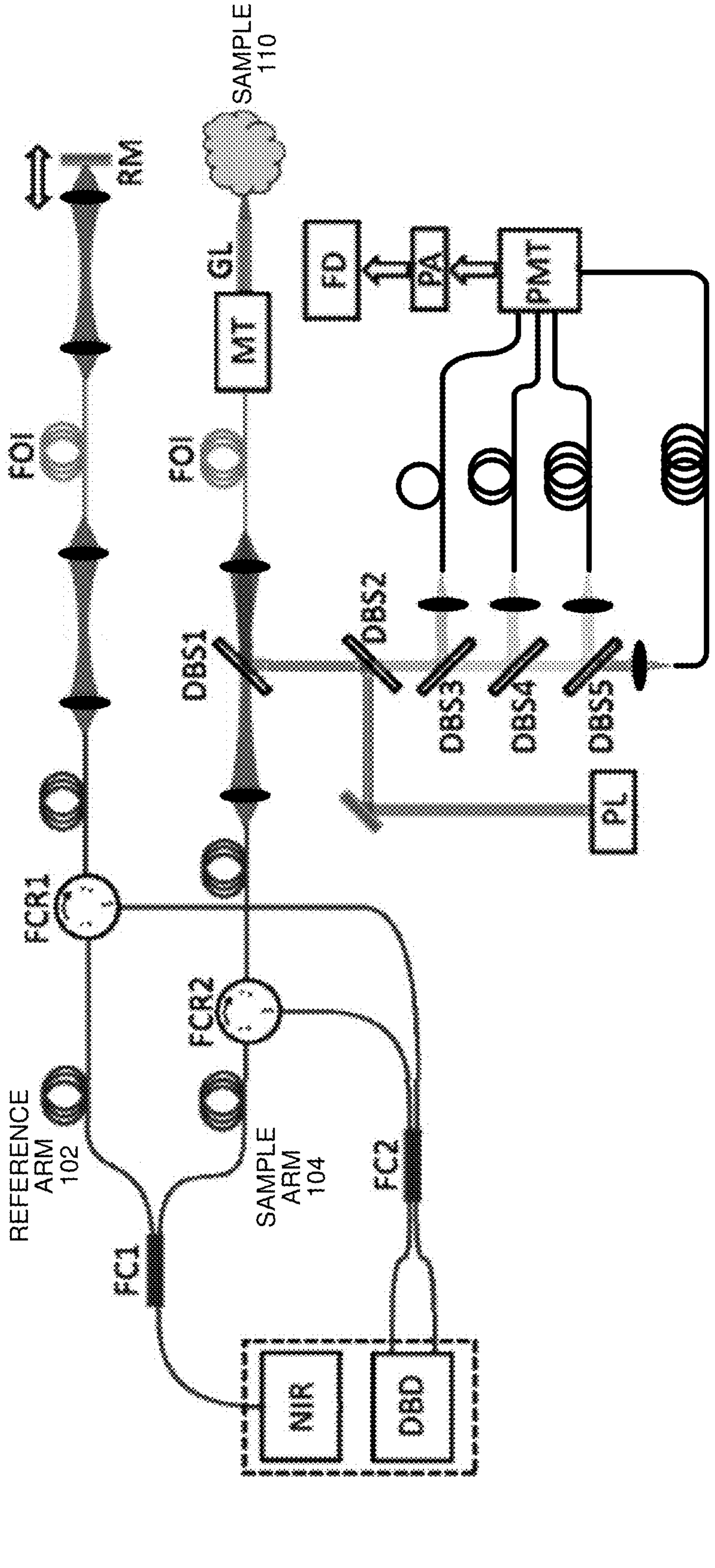
FIG. 1A presents a diagram of a simultaneous FLIm and OCT system in accordance with the disclosed embodiments.
Figure 1B:
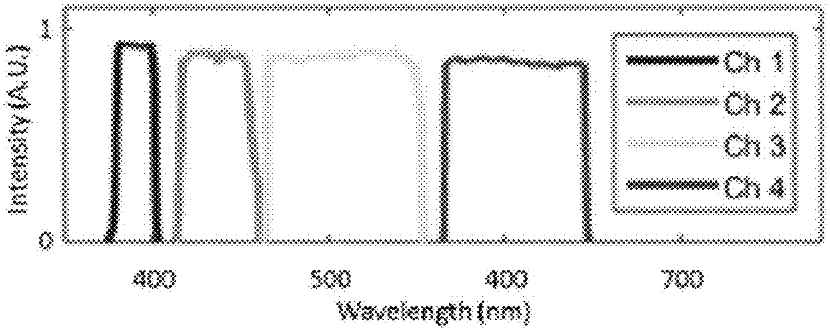
FIG. 1B illustrates a distribution of FLIm spectral bands in accordance with the disclosed embodiments.

The layout of the combined FLIm and OCT platform is shown in FIG. 1A. The FLIm system uses fiber-coupled, scanning multispectral time-resolved fluorescence spectroscopy, wherein the excitation source is a 355 nm pulsed microchip laser operating at 4 kHz. A pair of dichroic mirrors and an achromatic lens couple the laser pulses into the DCF inner cladding. Backscattered sample autofluorescence is collected in the DCF inner cladding and guided back to a custom wavelength selection module (WSM).

The WSM comprises three dichroic beam splitters (Semrock Di02-R405, FF458-Di02, FF555-Di03 produced by IDEX Health Sciences of Rochester, New York) and four band pass filters (Semrock FF01-390/18, FF01 435/40, FF01 510/85, FF01 607/70) that divide the light into four distinct spectral bands, which are referred to as channels (e.g., 'Channel 1' is used for the 390/18 nm spectral band). Light in each spectral band is coupled into a 600 μm core diameter fiber optic delay line, which is used to temporally multiplex the four spectral bands onto a single multichannel plate photomultiplier detector. The detector output is amplified and digitized using a low noise pre-amplifier and a high-speed data acquisition (DAQ) board, and lifetimes are extracted from the raw decays using a constrained least-squares deconvolution with Laguerre expansion technique.

The OCT imaging system is built around a 1310±55 nm swept source OCT (SSOCT) engine with an A-line rate of 50 kHz. The light source is fiber-coupled into a 90:10 fiber coupler FC1, which sends approximately 10% of the output, via a three-port fiber circulator FCR1 to the external interferometer reference arm 102 formed by a 2 m section of DCF and a metallic mirror mounted on a translation stage. The single-axis translation stage offers 100 mm of travel and is used to approximately match the optical path length of the sample and reference arms. The remaining 90% of the SSOCT light source output is coupled via another three-port fiber circulator FCR2 into the core of the same 2 meter section of DCF used for FLIm. This fiber realizes the external sample arm 104 for the OCT interferometer.

Reflections in both the sample arm 104 and reference arm 102 are coupled back through the DCFs, and are separated from the incoming light by the three-port fiber circulators FCR1 and FCR2. Light from each arm is mixed using a 50:50 fiber coupler FC1 and detected using a pair of dual balanced photodiodes. The SSOCT engine includes a high-speed field-programmable gate array (FPGA) data-acquisition board that processes data from the dual balanced detectors and generates depth resolved B-mode images, which are streamed via Ethernet connection to an experimental control computer.

FLIm and OCT images were acquired in parallel, and their acquisition were synchronized by a common TTL trigger at the start and end of each line. The generally low quantum yield of endogenous fluorophores motivated lifetimes to be extracted from the average of 16 consecutive fluorescence decays. Pre-processing of the FLIm data further reduced the effective acquisition rate of FLIm pixels to an average of 78 Hz. In order to avoid overfilling the SSOCT data-acquisition buffer, the effective acquisition rate of the OCT system was down-sampled to 500 Hz.

The working distance, axial collection efficiency and lateral point spread functions (PSF) of both imaging systems were estimated from measurements taken in air using a phantom fabricated from a 13 μm diameter tungsten wire coated with a thin layer of fluorescent dye. The phantom was imaged with FLIm (OCT) at 15 (12) different distances between the distal tip of the GRIN lens and the tungsten wire. The results of this analysis are shown in FIGS. 4A-4F. The working distance of the FLIm system was measured to be 4 mm. In the focal plane, the FLIm PSF full width at half maximum (FWHM) in the orthogonal x and y directions was measured to be 226.9 μm and 221.3 μm (See FIG. 4A). The high NA and large collection aperture of the DCF inner cladding allowed for a gradual decrease in the fluorescence collection efficiency with distance from the focal plane.

Figure 4A:
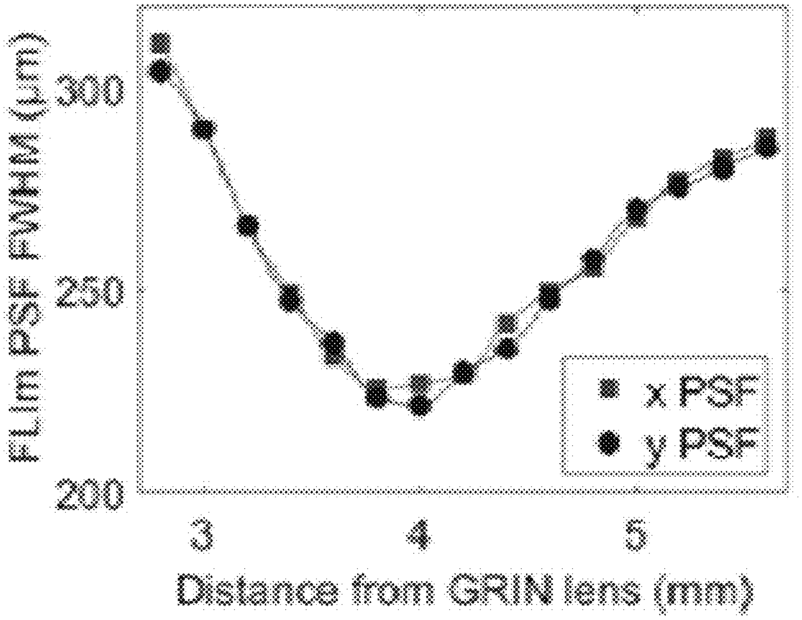
FIG. 4A presents a graph illustrating a FLIm lateral point spread function (PSF) full width at half maximum (FWHM) metric in accordance with the disclosed embodiments.
Figure 4B:
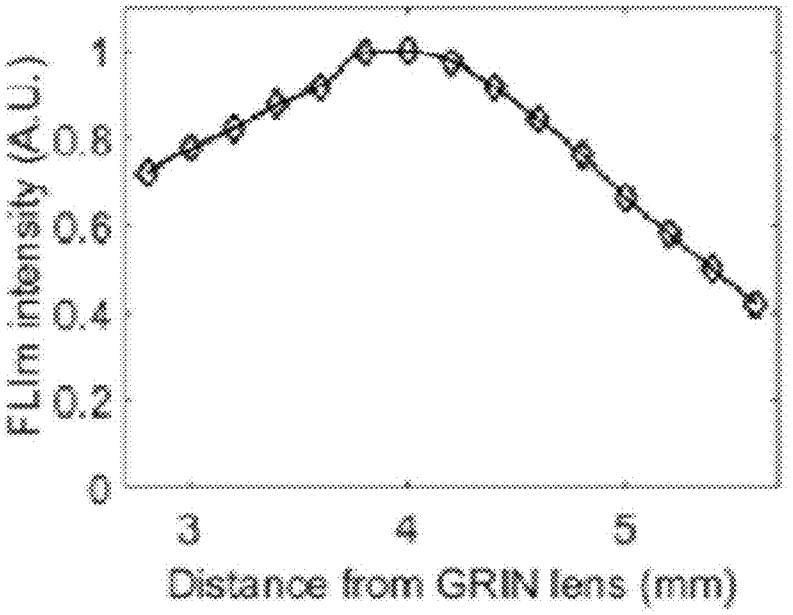
FIG. 4B presents a graph illustrating FLIm on-axis normalized collection efficiency in accordance with the disclosed embodiments.
Figure 4C:
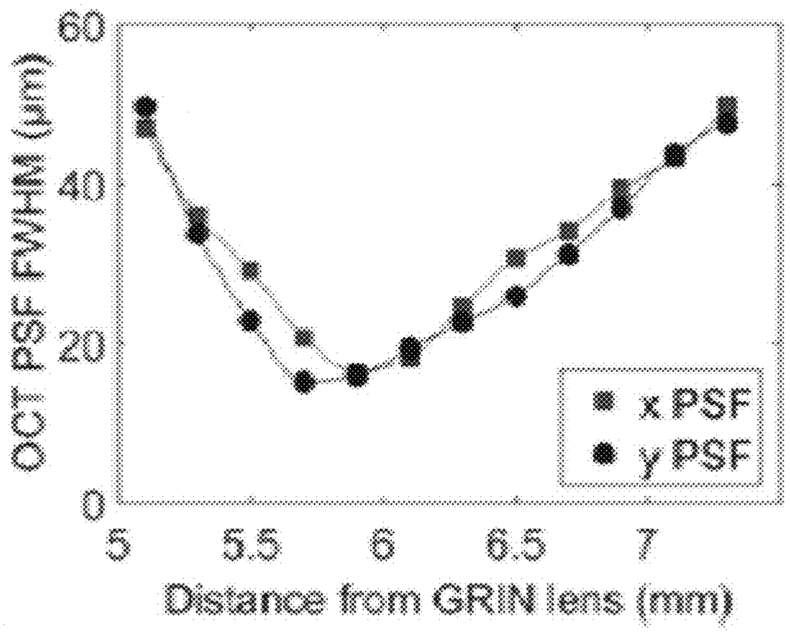
FIG. 4C presents a graph illustrating a OCT lateral PSF FWHM metric in accordance with the disclosed embodiments.
Figure 4D:
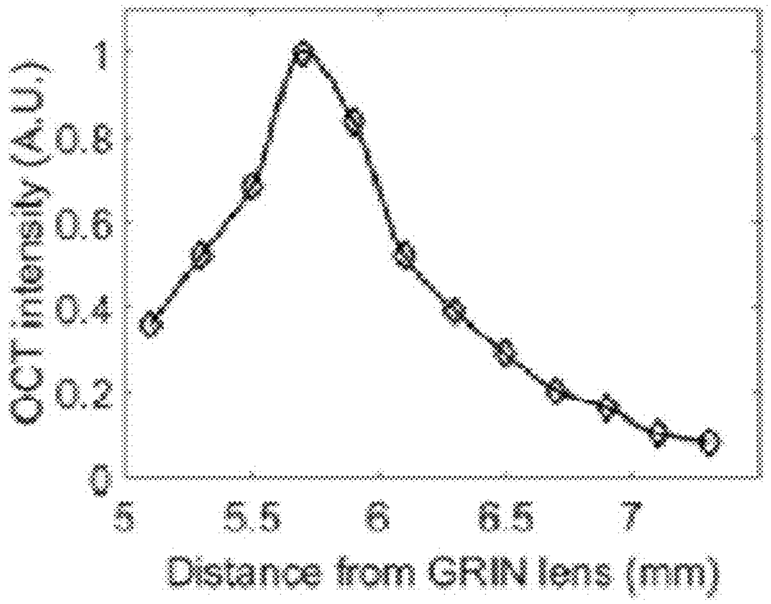
FIG. 4D presents a graph illustrating OCT on-axis normalized collection efficiency in accordance with the disclosed embodiments.
Figure 4E:
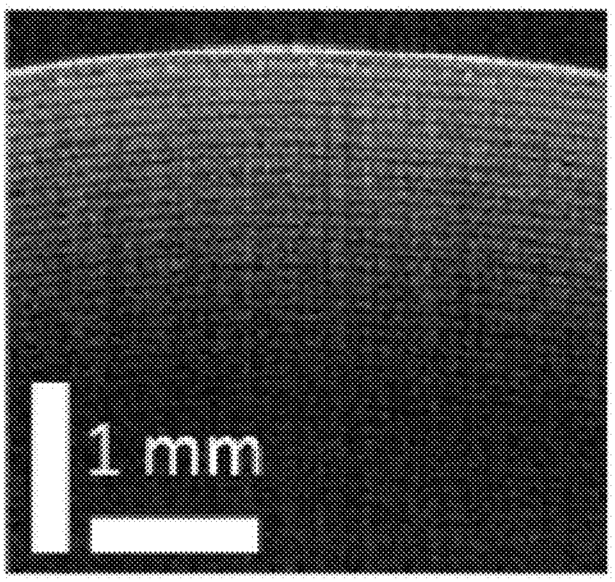
FIG. 4E presents a graph illustrating an OCT B-scan of a roll of scotch tape in accordance with the disclosed embodiments.
Figure 4F:
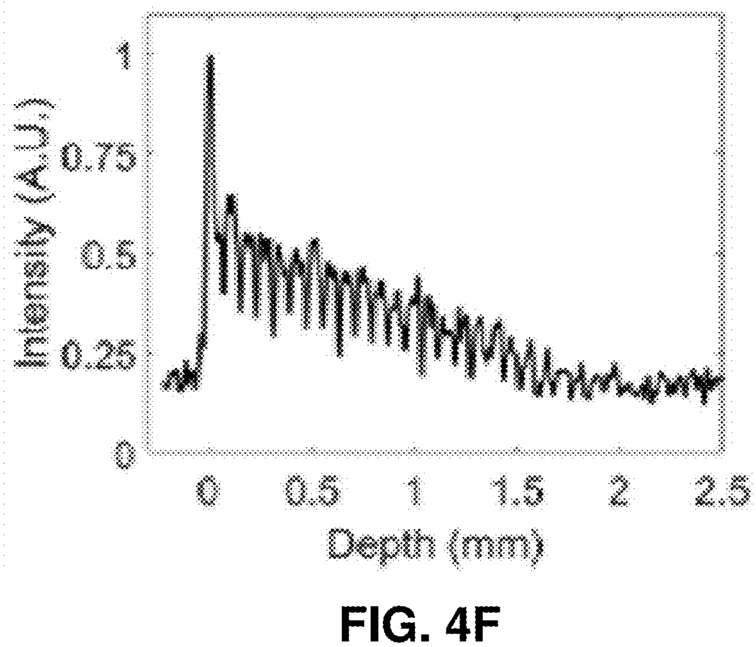
FIG. 4F presents a graph illustrating a mean of 10 neighboring OCT A-lines from FIG. 4E in accordance with the disclosed embodiments.

As is shown in FIG. 4B, the fluorescence intensity only falls to half its maximum value at 1.4 mm below the focal plane. While the penetration depth of 355 nm light in tissue is typically limited to less than 200 μm by absorption, the slow decay of axial fluorescence collection efficiency lessens the impact of chromatic focal shift in the GRIN lens and allows the sample surface to be positioned at a distance, which is optimized for the OCT system. For OCT, uncorrected chromatic aberration in the GRIN lens increased the working distance of the OCT system to 5.7 mm. In the focal plane, the PSF FWHM were measured to be 16.3 μm and 16.0 μm in the x and y directions, respectively (see FIG. 4C). The FWHM of the OCT axial collection efficiency was measured to be 1.8 mm (see FIG. 4D). The size of the axial PSF for OCT was estimated from measurements of an image of a microscope slide. The axial PSF FWHM was measured to be 10.2 μm, which agrees with the theoretical value derived from the coherence length of the light source. Using a scotch tape phantom (see FIG. 4E), it was observed that the OCT system was able to image features approximately 1.8 mm below the sample surface (see FIG. 4F). Images of a protected silver mirror were used to calculate the sensitivity of the OCT system to be 92 dB (data not shown).

Figure 5A:
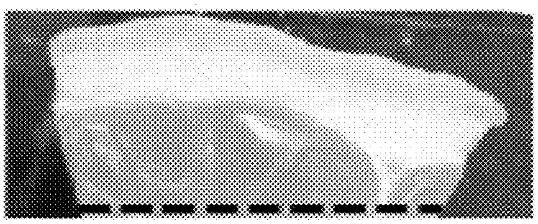
FIG. 5A presents a white light image of an 18×8 mm lemon segment in accordance with the disclosed embodiments.
Figure 5B:
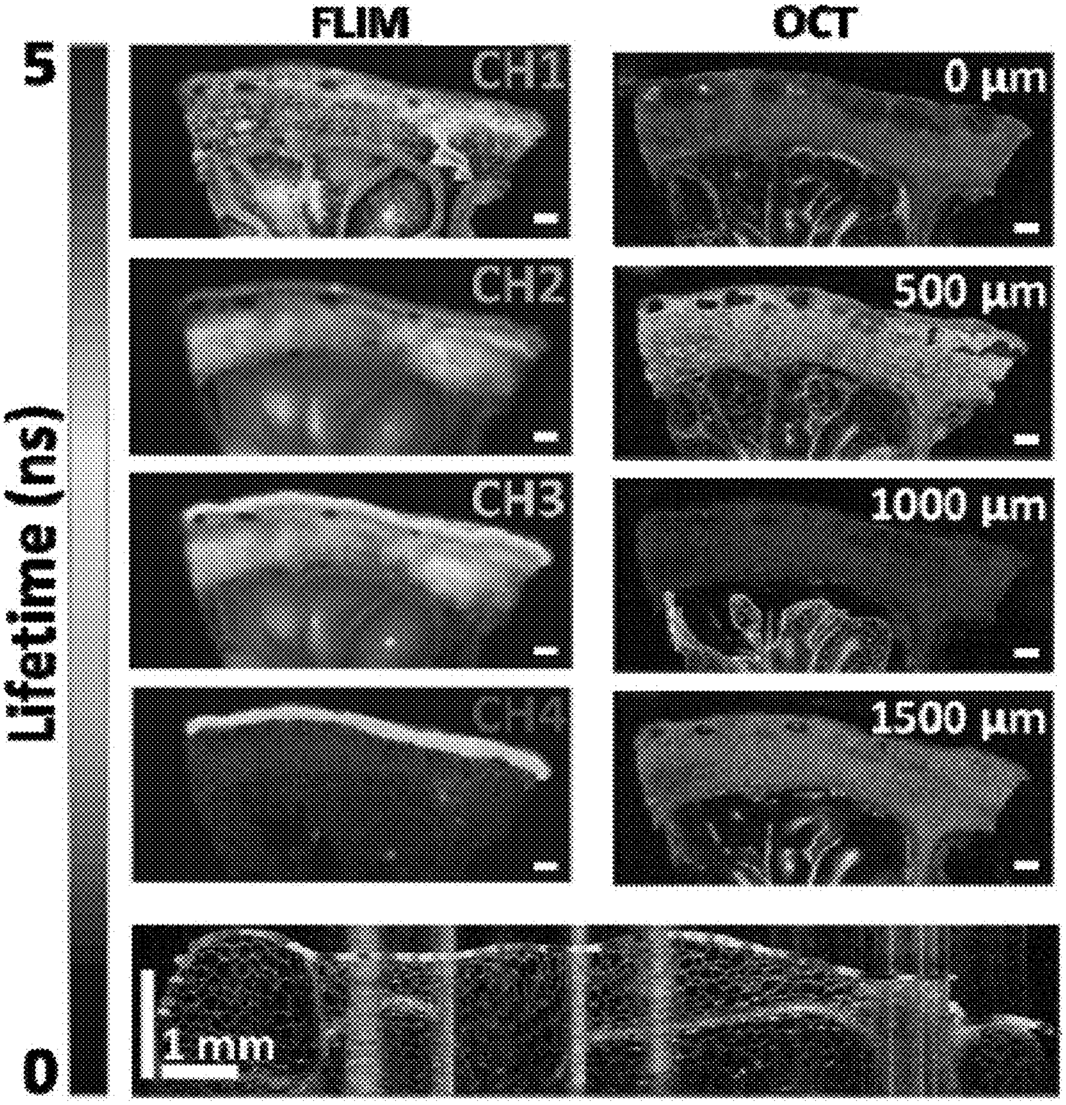
FIG. 5B presents FLIm and OCT images of the lemon segment in accordance with the disclosed embodiments.

The ability of the FLIm and OCT platform to simultaneously acquire images containing biochemical and structural contrast was first tested by imaging an 18×8 mm lemon segment (see FIGS. 5A-5B). The fluorescence lifetime images show the same field of view, resolved into the four distinct spectral bands. Stark regions of contrast are observed in these images, such as in the shortest wavelength spectral band (CH1) where the walls of the juice sacks and their contents show significantly different fluorescence lifetimes. The OCT images depict the microstructure of the lemon segment at four different depths below the sample surface. The significantly higher spatial resolution of OCT allows this modality to resolve individual plant cells, as can be seen in the cross-sectional image at the bottom of FIG. 5B.

Figure 6A:
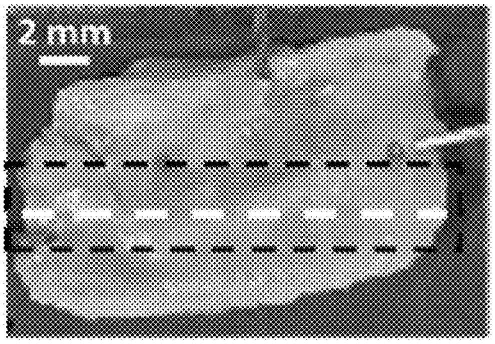
FIG. 6A presents a white light image of an 18×9 mm coronary artery section in accordance with the disclosed embodiments.
Figure 6B:
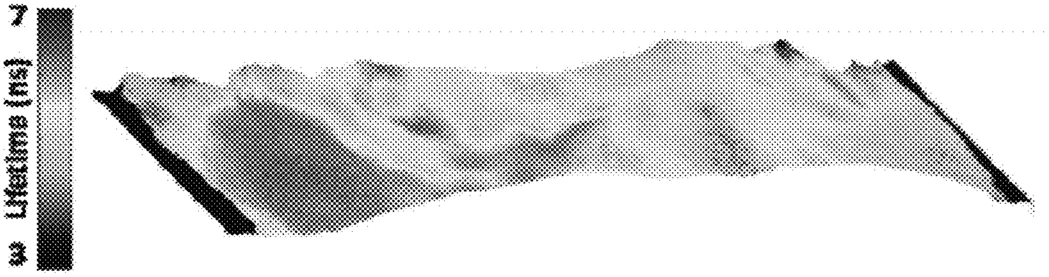
FIG. 6B illustrates a spatial distribution of fluorescence lifetimes acquired in the 390/18 nm from an 18×4 nm coronary artery section spectral band in accordance with the disclosed embodiments.
Figure 6C:
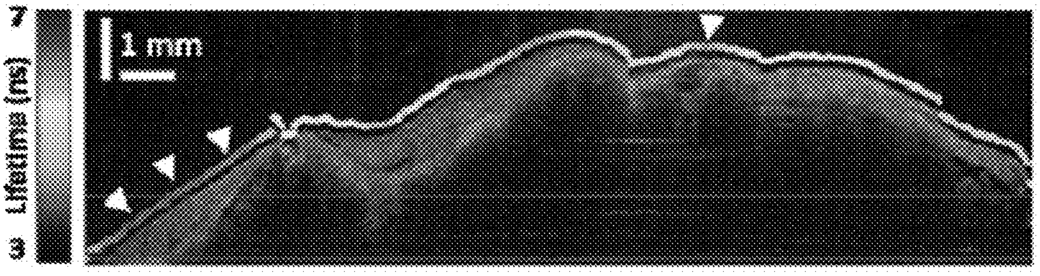
FIG. 6C presents a line scan across the artery sample showing fluorescence lifetime data in accordance with the disclosed embodiments.

A further test of the simultaneous FLIm and OCT platform was provided by an 18×9 mm section of human coronary artery (of which an 18×4 mm section was imaged). The artery was cut along the direction of blood flow and pinned to a silicone rubber sheet to provide an approximately flat surface for the FLIm and OCT system to image. A white light image of the artery section in its imaging configuration is shown in FIG. 6A. The spatial distribution of fluorescence lifetime in CH1 is plotted as a function of the surface height extracted from the OCT data in FIG. 6B. Finally, in FIG. 6C the fluorescence lifetime data from a single line scan across the sample (the white dashed line in FIG. 6A) has been written on to the surface of the corresponding OCT B-scan. The white arrow heads in this image indicate the coincidence of regions of contrast detected by the two different modalities. The three arrowheads on the left side of the image show the alignment of a region of longer fluorescence lifetime, and a homogeneous region of low attenuation and high reflectivity.

Although the absence of co-registered histology images makes a definite diagnosis of this region of the tissue not possible, previous studies have shown that these features have a strong association with regions of fibrotic tissue. Similarly, the single arrow head on the centre right of the image shows an overlap of a region of shorter fluorescence lifetime with a region of low OCT reflectivity. Note that this work can be extended to generate an image classifier, which uses processed data from both FLIm and OCT to identify tissue features of interest with a higher sensitivity and specificity than could be achieved using a single modality.

Dual-Resolution Feature

Figure 8A:
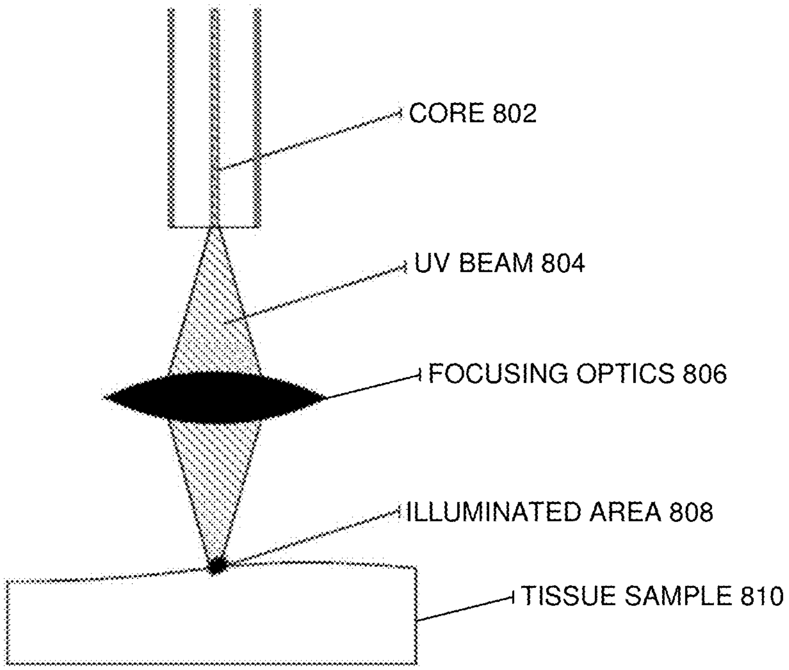
FIG. 8A illustrates a high-resolution optical imaging mode, which is based on fluorescence excitation through the optical core of the double-clad optical fiber in accordance with the disclosed embodiments.
Figure 8B:
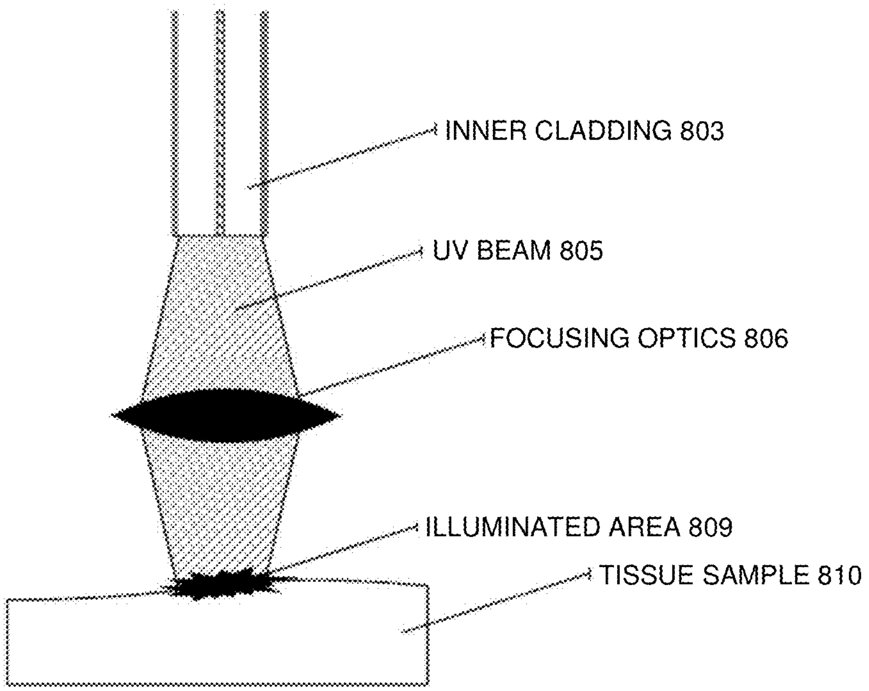
FIG. 8B illustrates a low-resolution optical imaging mode, which is based on fluorescence excitation through the inner cladding of the double-clad optical fiber in accordance with the disclosed embodiments.

In some embodiments, the disclosed embodiments support a dual-resolution feature, wherein fluorescence excitation is provided through different light-guiding regions in the double-clad optical fiber to provide respective high-resolution and low-resolution imaging modes as is illustrated in FIGS. 8A and 8B. More specifically, FIG. 8A illustrates a high-resolution optical imaging mode, which is based on channeling fluorescence excitation transmitted through the optical core 802 of the double-clad optical fiber to provide a UV beam 804, which is directed through focusing optics 806 onto an illuminated area 808 of a tissue sample 810. In contrast, FIG. 8B illustrates a low-resolution optical imaging mode, which is based on fluorescence excitation transmitted through the inner cladding 803 of the double-clad optical fiber to provide wider a UV beam 805, which is similarly directed through focusing optics 806 onto a larger illuminated area 809 of a tissue sample 810.

Process of Operation

FIG. 7 presents a flow chart for the process of operating a combined FLIm and OCT imaging system, which transmits light through a single optical fiber, in accordance with the disclosed embodiments. During operation, the system uses a fiber-coupled fluorescence imaging system, which operates based on ultra-violet (UV) excitation light, to gather a fluorescence emission from a sample-of-interest (step 702). The system also concurrently uses a fiber-coupled optical coherence tomography (OCT) imaging system to acquire depth-resolved images of the sample-of-interest (step 704). During operation of the combined system, light for both fluorescence imaging and OCT imaging is directed through a single double-clad optical fiber, which facilitates light delivery to the sample-of-interest and collection of associated returned optical signals (step 706). This single optical fiber carries both UV light for the fluorescence imaging and infrared light for the OCT imaging through two concentric light-guiding regions, thereby facilitating generation of precisely co-registered optical data from the fluorescence imaging system and the OCT imaging system.

CONCLUSION

We successfully acquired results using a novel fiber-based, multimodal imaging system that combines FLIm with OCT. This system operates entirely label-free and is able to acquire images of structural and biochemical contrast from biological samples. The use of a double-clad optical fiber as an interface between the apparatus and sample presents the opportunity to employ this imaging platform in regions where conventional free-space optics-based imaging systems cannot operate.

Various modifications to the disclosed embodiments will be readily apparent to those skilled in the art, and the general principles defined herein may be applied to other embodiments and applications without departing from the spirit and scope of the present invention. Thus, the present invention is not limited to the embodiments shown, but is to be accorded the widest scope consistent with the principles and features disclosed herein.

The foregoing descriptions of embodiments have been presented for purposes of illustration and description only. They are not intended to be exhaustive or to limit the present description to the forms disclosed. Accordingly, many modifications and variations will be apparent to practitioners skilled in the art. Additionally, the above disclosure is not intended to limit the present description. The scope of the present description is defined by the appended claims.

What is claimed is:

1. A multimodal imaging system for simultaneously acquiring images of tissue structure and function with a single optical fiber, comprising:

a fiber-coupled fluorescence imaging system operating with ultra-violet (UV) excitation light;

a fiber-coupled optical coherence tomography (OCT) imaging system;

a fiber optic interface including a single optical fiber, which facilitates light delivery to a sample-of-interest and collection of returned optical signals, for both the fluorescence imaging system and the OCT imaging system, wherein:

the single optical fiber comprises:

a central core; and a multimode inner cladding;

both UV excitation light for the fluorescence imaging system and infrared light for the OCT imaging system are transmitted through the central core to enable fluorescence lifetime imaging (FLIm); and returned light for the fluorescence imaging system is transmitted;

a wavelength selection module that includes:

N dichroic beam splitters, wherein N>1;

N+1 band-pass filters that divide the returned light into N+1 distinct spectral bands;

a multichannel photomultiplier detector; and a multiplexer that temporally multiplexes the N+1 distinct spectral bands onto the multichannel photomultiplier detector;

a pre-amplifier that amplifies output of the multichannel photomultiplier; and a data acquisition board that digitizes output of the pre-amplifier;

wherein lifetimes of the N+1 distinct spectral bands of the returned light for the FLIm imaging are extracted from raw decays.

2. The multimodal imaging system of claim 1, wherein the single optical fiber is a double-clad fiber comprising:

the central core composed of pure silica, surrounded by a ring of low-index doped silica;

the multimode inner cladding composed of pure silica surrounding the central single-mode core; and an outer cladding surrounding the multimode inner cladding and composed of a low-index material comprising doped silica or a low-index polymer.

3. The multimodal imaging system of claim 1, wherein the fluorescence imaging system comprises a time-resolved fluorescence lifetime imaging FLIm system.

4. The multimodal imaging system of claim 1, wherein the UV excitation light has a wavelength less than 400 nm.

5. The multimodal imaging system of claim 1, wherein the fiber-coupled fluorescence imaging system and the fiber-coupled optical coherence tomography imaging system of the multimodal imaging system provide an optical architecture that allows structural and functional imaging modalities to operate independently and in parallel.

6. The multimodal imaging system of claim 1, wherein the fiber-coupled fluorescence imaging system and the fiber-coupled optical coherence tomography imaging system of the multimodal imaging system provide an optical architecture that facilitates switching between different optical resolutions.

7. A method of performing multimodal imaging to simultaneously acquire images of tissue structure and function with a single optical fiber, the method comprising:

operating a fiber-coupled fluorescence lifetime imaging (FLIm) system that uses ultra-violet (UV) excitation light;

concurrently operating a fiber-coupled optical coherence tomography (OCT) imaging system; and during the concurrent operation of the FLIm system and the OCT imaging system, directing light to and from the FLIm system and the OCT imaging system though a fiber optic interface comprising a single optical fiber that facilitates light delivery to a sample-of-interest and collection of associated returned optical signals for both the FLIm system and the OCT imaging system;

receiving returned light for the FLIm system from the sample-of-interest via the multimode inner cladding;

dividing the returned light into multiple spectral bands;

temporally multiplexing the multiple spectral bands onto a multichannel photomultiplier detector;

amplifying and digitizing output of the multichannel photomultiplier detector; and extracting lifetimes of the multiple spectral bands for the fluorescence lifetime imaging from raw decays;

wherein the single optical fiber comprises:

a central core; and a multimode inner cladding; and wherein both UV excitation light for the FLIm system and infrared light for the OCT imaging system are transmitted through the central core.

8. The method of claim 7, wherein the single optical fiber is a double-clad fiber comprising:

the central core composed of pure silica, surrounded by a ring of low-index doped silica;

the multimode inner cladding composed of pure silica surrounding the central single-mode core; and an outer cladding surrounding the multimode inner cladding and composed of a low-index material comprising doped silica or a low-index polymer.

9. The method of claim 7, wherein the fluorescence imaging system comprises a time-resolved fluorescence lifetime imaging (FLIm) system.

* * * * *